United States Patent [19]

Sawai et al.

[11] Patent Number: 5,560,925

[45] Date of Patent: Oct. 1, 1996

[54] METHOD OF TREATING WART

[75] Inventors: Kiichi Sawai; Takahiko Mitani; Naohisa Ninomiya; Yoshiro Ishiwata, all of Nagoya, Japan

[73] Assignee: Sanwa Kagaku Kenkyusho Co., Ltd., Aich-ken, Japan

[21] Appl. No.: 316,848

[22] Filed: Oct. 3, 1994

[51] Int. Cl.⁶ ....................................... A61K 9/20
[52] U.S. Cl. .................... 424/464; 424/465; 514/777; 514/781
[58] Field of Search ........................ 424/464, 465, 424/78.37, 184, 492, 499; 514/650, 777, 781

[56] References Cited

U.S. PATENT DOCUMENTS

| | | | |
|---|---|---|---|
| 4,889,715 | 12/1989 | Sawai et al. | 514/184 |
| 5,008,416 | 4/1991 | Kurono et al. | 424/650 |
| 5,180,739 | 1/1993 | Sawai et al. | 514/492 |
| 5,240,700 | 8/1993 | Sawai et al. | 424/78.37 |
| 5,260,056 | 11/1993 | Sawai et al. | 424/650 |
| 5,279,835 | 1/1994 | Sawai et al. | 424/464 |
| 5,336,688 | 8/1994 | Sawai et al. | 424/78.08 |
| 5,340,806 | 8/1994 | Sawai et al. | 514/492 |

OTHER PUBLICATIONS

Hurukuni, Tokuda, Oyo Yakuri (1993), 46(1), pp. 39–43. (English Abstract Provided).

*Primary Examiner*—Thurman K. Page
*Assistant Examiner*—Pamela S. Webber
*Attorney, Agent, or Firm*—Sughrue, Mion, Zinn, Macpeak & Seas

[57] ABSTRACT

Wart of human being is prevented or cured by administration of a pharmaceutical composition containing an eight structural polymer of 2-oxygermylpropionic acid having an empirical formula of $C_6H_{10}Ge_2O_7$, a minimum constitutional unit of $(O_{1/2})_3GeCH_2CH_2COOH$ and the following stereostructure:

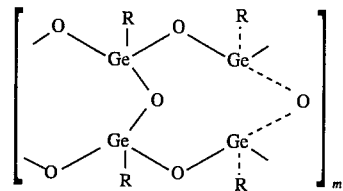

wherein R stands for —$CH_2CH_2COOH$ and m is an integer of $137\pm84$.

4 Claims, No Drawings

METHOD OF TREATING WART

BACKGROUND OF THE INVENTION

1. Field of the Invention

This invention relates to a method of treating or preventing wart of human being.

2. Description of the Prior Art

3-Oxygermylpropionic acid which undergoes polymerization in a complicated manner is useful for various applications. In particular, because of the specific pharmacological activities, 3-oxygermylpropionic acid compounds have now attracted attention of many researchers. Japanese Examined Patent Publication No. 57-53800 discloses antiviral activities of such compounds.

Carboxyethylgermanium sesquioxide, generally called Ge132, is known to have a twelve-membered ring structure (J. Am. Chem. Soc., 98 (25), 8287 (1976)).

The known organogermanium compounds, however, have a problem that it is difficult to synthesize the compounds with good reproducibility. Thus, the pharmacological activities of the known compounds vary from lot to lot. Additionally, the known compounds encounter a problem because the activities are lowered during dispensing or storage.

The present inventors have proposed effective stabilizing agents for 3-oxygermylpropionic acid (Japanese Unexamined Patent Application No. 61-65819) and also found that sugar serves to enhance the pharmacological activities of the acid (Japanese Unexamined Patent Application No. 60-190714).

SUMMARY OF THE INVENTION

It is an object of the present invention to provide a method of treating or preventing wart, especially verruca caused by virus belonging to a papova virus group.

In accomplishing the foregoing objects, there is provided in accordance with the present invention a method of treating or preventing wart of a subject, comprising administrating to the subject a pharmacologically effective amount of a composition containing an organogermanium compound having an empirical formula of $C_6H_{10}Ge_2O_7$, a minimum constitutional unit of $(O_{1/2})_3GeCH_2CH_2COOH$ and the following stereostructure:

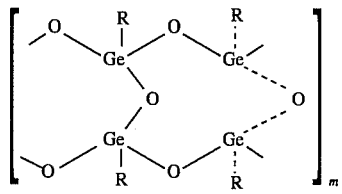

wherein R stands for $-CH_2CH_2COOH$ and m is an integer of 137±84.

In another aspect, the present invention provides the use of the above organogermanium compound for therapeutic treatment or prevention of wart of human being.

The present inventors have found that compounds expressed by the formula $[(O_{1/2})_3GeCH_2CH_2COOH]_n$ include three groups with different stereostructures. One of the three groups includes the compound of the present invention and shows higher activities than the other two groups.

The chemical and physical properties of the compound according to the present invention (hereinafter referred to as OGP-8) are as summarized in Tables 1 and 2. Table 1 shows the results of the molecular weight measurement by the light scattering method while Table 2 shows the lattice constant determined by the powder X-ray diffraction method.

TABLE 1

| Weight Average | OGP-8 Propyl Ester | OGP-8 (equivalent value) |
|---|---|---|
| Molecular Weight (Mw) | | |
| Average (X) | $1.16 \times 10^5$ | $9.29 \times 10^4$ |
| Standard deviation 3 | $\pm 0.71 \times 10^5$ | $\pm 5.72 \times 10^4$ |
| Molecular Formula* | $(C_6H_{11}GeO_{3.5})_n$ | $(C_3H_5GeO_{3.5})_n$ |
| Weight Average Polymerization Degree (n)* | 548 ± 337 | 548 ± 337 |

*n is an integer determined provided that the minimum constitutional unit of OGP-8 is $(O_{1/2})_3GeCH_2CH_2COOH$

TABLE 2

| | |
|---|---|
| Chemical formula *1 | $C_3H_5GeO_{3.5}$ |
| Formula weight *1 | 169.66 |
| Crystal class | monoclinic |
| Space group | — |
| Unit cell parameters | |
| a (Å) | 13.35 (1) |
| b (Å) | 5.03 (1) |
| c (Å) | 7.55 (2) |
| β (deg.) | 94.3 (2) |
| vol (Å³) | 505.4 *2 |
| z | 4 *3 |
| Density (gcm⁻³) | 2.23 *4 |

*1: indicated provided that the minimum constitutional unit of OGP-8 is $(O_{1/2})_3GeCH_2CH_2COOH$
*2: calculated on the basis of the lattice constants
*3: calculated on the basis of lattice constants and the measured density
*4: measured by the floating method Table 3 shows a side by side comparison of the physical properties between OGP-8 and Ge-132.

TABLE 3

| | OGP-8 | Ge-132 |
|---|---|---|
| 1 | H = 3.02%, C = 21.10% | H = 3.01%, C = 21.15% |
| 2 | $\lambda_{max}$ = 192.5 nm, $E_{1\ cm}^{1\%}$ = 3.73 | $\lambda_{max}$ = 192.5 nm, $E_{1\ cm}^{1\%}$ = 3.75 |
| 3 | 1696 cm⁻¹, 1435 cm⁻¹, 1265 cm⁻¹, 890 cm⁻¹, 805 cm⁻¹ | 1690 cm⁻¹, 1410 cm⁻¹, 1240 cm⁻¹, 905 cm⁻¹, 790 cm⁻¹, 730 cm⁻¹ |
| 4 | 456 cm⁻¹ | 449 cm⁻¹ |
| 5 | 2θ = 6.5°, 11.6°, 13.7°, 21.0°, 22.3° | 2θ = 7.8°, 15.5°, 19.2°, 20.6°, 22.0°, 26.0° |

TABLE 3-continued

| | OGP-8 | Ge-132 |
|---|---|---|
| 6 | δppm (D$_2$O):<br>2.69(2H, t, J=7.6,<br>Ge—CH$_2$—C̲H̲$_2$—)<br>1.61(2H, t, J=7.6,<br>Ge—C̲H̲$_2$—CH$_2$—) | δppm (D$_2$O):<br>2.69(2H, t, J=7.6,<br>Ge—CH$_2$—C̲H̲$_2$—)<br>1.61(2H, t, J=7.6,<br>Ge—C̲H̲$_2$—CH$_2$—) |
| 7 | δppm:<br>181.87(Ge—CH$_2$—CH$_2$—C̲OOH)<br>28.24, 29.79, 30.86<br>(Ge—C̲H̲$_2$—CH$_2$—COOH)<br>18.38, 18.95, 18.41<br>(Ge—CH$_2$—C̲H̲$_2$—COOH) | δppm:<br>181.30(Ge—CH$_2$—CH$_2$—C̲OOH)<br>28.43(Ge—C̲H̲$_2$—CH$_2$—COOH)<br>15.68 (Ge—CH$_2$—C̲H̲$_2$—COOH) |
| 8 | peak apex 252° C.<br>ΔH 48.4 mcal/mg | peak apex 189° C., 282° C.<br>ΔH 46.8 mcal/mg |
| 9 | needle crystals | amorphous |
| 10 | 1.57% | 1.17% |

Remarks:
1: Elementary analysis,
2: UV spectrum,
3: IR spectrum,
4: Raman spectrum,
5: Powder X-ray diffraction pattern,
6: $^1$H NMR spectrum (liquid),
7: $^{13}$C NMR (solid),
8: DSR,
9: Crystal form,
10: Solubility Other objects, features and advantages of the present invention will become apparent from the detailed description of the preferred embodiments of the invention to follow.

DETAILED DESCRIPTION OF THE PREFERRED EMBODIMENTS OF THE INVENTION

The pharmaceutical composition containing OGP-8 may be any desired form such as a tablet or a capsule. It is preferred that OGP-8 be used in conjunction with a carrier for stabilizing the phamacological activity thereof. Examples of suitable carriers include sugar such as lactose, sucrose and dextran; modified cellulose such as hydroxypropylcellulose; and naturally occurring polymers such as albumin. The carrier is generally used in an amount of 0.001 to 1,000 parts by weight per part by weight of OGP-8. If desired, the composition may additionally contain a drug which is generally used for curing immune diseases. Illustrative of suitable drugs are antiviral agents for viral hepatitis, antiallergic agents for allergic diseases and anticancerous agents for cancer. By using such a drug in combination with OGP-8, the toxicity of the drug may be relieved while maintaining the curative activities high. Depending upon the type of the drug, the pharmaceutical composition may be formulated into an enteril form.

The composition of the present invention is generally administered to humans at a dose of 1–1,500 mg/day, though the dose is variable depending upon the type or form of the composition, the age of patients, etc. In the case of adults (weighing 50 kg), for example, the dose is preferably 1–150 mg/day.

The following examples will further illustrate the present invention.

EXAMPLE 1

Preparation of OGP-8

In 2 liters of ethanol were dissolved 252 g (1 mole) of 3-trichlorogermylpropionic acid to obtain a solution, to which 1.5 liters of water were slowly added while maintaining the mixture at 20° C. It took several hours to completely add the water. The mixture was allowed to stand for 24 hours and the precipitates were then separated by filtration, washed with acetone and dried under vacuum, thereby to obtain OGP-8 with a yield of 90%. The molecular weight and the lattice constant of OGP-8 are shown in Tables 1 and 2 above.

EXAMPLE 2

Composition in the Form of Tablet

Using ethanol as a wetting agent, 2 parts by weight of OGP-8 and 1 part by weight of hydroxypropylcellulose were kneaded together. The kneaded blend was then dried at 50° C. or less to obtain a powdery or granular mixture. This mixture was blended with the following ingredients and the blend was tableted in a conventional manner.

| | |
|---|---|
| Mixture containing OGP-8 | 10.0 mg |
| Lactose | 159.2 mg |
| Carboxymethylcellulose (Na) | 8.0 mg |
| Soft silica | 2.0 mg |
| Magnesium stearate | 1.8 mg |
| | 180.0 mg/tablet |

EXAMPLE 3

Pharmacological Test

Seven-age BALB/c mice were each subcutaneously transplanted with 2×10$^6$ Sarcoma-180 cells. Nine days after the transplantation, OGP-8 was daily per os administered to the mice at doses of 0.3, 1, 3, 10 and 30 mg/kg/day for five days. The next day after the completion of the medication, each mouse was sensitized with 2×10$^8$ sheep red blood corpuscles (SRBC) by intravenous injection. Four days after the sensitization, the spleen of each mouse was enucleated to measure the amount of SRBC IgM-PFC in the cell.

For the purpose of comparison, the above procedure was repeated in the same manner as described except that Ge132 (carboxyethylgermanium sesquioxide) was used in lieu of OGP-8.

The results were as summarized in Table 4. As seen from Table 4, a dosage of 0.3 mg/kg of OGP-8 can significantly recover the ability of the cancer-bearing mice to produce the antibody. The PFC number becomes maximum with a dosage of 1–3 mg/kg. Significant antibody production-enhancing effect is obtainable with a dosage of up to 10 mg/kg. In contrast, with G132, significant effect is obtainable only when the dosage is 30 mg/kg. Thus, it is appreciated that OGP-8 is effective in increasing the antibody producing ability of the animals which has been lowered due to cancer and that OGP-8 is about 100 times as effective as Ge132.

TABLE 4

| | Dosage (mg/kg) | IgM-PFC Number/ $10^6$ Spleen Cell |
|---|---|---|
| Normal Mice Group (control) | — | 1,613 ± 107*** |
| Cancer Mice Group (control) | — | 740 ± 40 |
| OGP-8-Dosed Mice Group | 0.3 | 984 ± 61** |
| | 1 | 1,269 ± 112*** |
| | 3 | 1,258 ± 82*** |
| | 10 | 1,004 ± 102* |
| | 30 | 909 ± 64* |
| Ge132-Dosed Mice Group | 0.3 | 770 ± 77 |
| | 1 | 779 ± 63 |
| | 3 | 805 ± 97 |
| | 10 | 826 ± 60 |
| | 30 | 995 ± 69** |

IGM-PFC number is an average in 7 mice ± standard deviation.
Significance:
$p < 0.01$, *$p < 0.001$

EXAMPLE 4

Pharmacological Test

The action of OGP-8 on preventing and curing wart was examined. House rabbit (Japanese white rabbit) was used to investigate the action of OGP-8 on induction and formation of papilloma by shope papilloma virus (SPV).

Groups of female white rabbits were used for the test. Each group consisted of seven rabbits each weighing 2–2.5 kg. A papilloma tissue was homogenized in a phosphate buffer (pH: 7.2) saline solution (20 g tissue were used per 100 ml saline solution) to obtain an infective virus liquid. The shaved skin of each rabbit was inoculated with the SPV liquid at four portions each having a size of 20 mm×20 mm by the sacrification method. Given amounts (0.3, 1, 3, 10 and 30 mg/kg a day) of OGP-8 contained in capsules were per os administrated to respective groups of rabbits on the day of the inoculation and, thereafter, twice a week over 10 weeks. After 5 and 10 weeks from the initiation of the administration, the volume of papilloma was measured in terms of the product of A×B×C where A, B and C represent the major axis, minor axis and height, respectively, of papilloma. The papilloma volume is an average volume of the papilloma in the four inoculated portions of each rabbit. The results are summarized in Table 5. Each value in Table 5 is an average of the papilloma volumes in each group (seven rabbits)±standard variation.

TABLE 5

| | Volume of Papilloma | |
|---|---|---|
| | 5 weeks | 10 weeks |
| Control | 7.7 ± 0.9 | 13.8 ± 1.5 |
| 0.3 mg/kg | 5.5 ± 0.9 | 5.4 ± 0.9** |
| 1 mg/kg | 3.3 ± 0.5** | 2.4 ± 0.5*** |
| 3 mg/kg | 2.1 ± 0.6*** | 2.8 ± 0.7*** |
| 10 mg/kg | 3.2 ± 0.3** | 4.0 ± 0.4*** |
| 30 mg/kg | 4.5 ± 0.9* | 7.9 ± 1.3* |

Significance relative to control:
*$p < 0.05$, $p < 0.01$, *$p < 0.001$

As seen from Table 5, a dosage of 1–30 mg/kg of OGP-8 shows significant effect of the inhibition of the formation of papilloma 5 weeks after the start of the administration. The inhibition effect becomes more prominent after 10 weeks administration and becomes maximum with a dosage of 1–3 mg/kg. In the group of the 1 mg/kg dosage, there were found rabbits in which the papilloma was almost retracted. No weight reduction was observed even in the rabbits with the maximum dosage (30 mg/kg).

EXAMPLE 5

Clinical Test

Examined in this test is the efficancy of OGP-8 against verruca plana juvenilis which is caused by infection of human papilloma virus. It is known that immunity has a great part in the occurence and the course of cure of verruca *plama juvenilis*.

Twenty patients infected with verruca plana juvenilis were each dosed with 10 mg of OGP-8 after each meal three times a day. The dosage was continued for 2 weeks in principle. However, the dosage was immediately stopped for patients who were diagnosed by the physician in charge as being complete cure. Each patient was diagnosed for the over-all judgement by the physician in charge. The results after the 2 weeks dosage are summarized in Table 6. As will be seen from the results in Table 6, OGP-8 exhbits high curative effect on verruca plama juvenilis. No side effects were observed during the dosage of OGP-8.

TABLE 6

| Curative Effect | Case Number |
|---|---|
| Cure | 13 (65%) |
| Alleviation | 5 (25%) |
| No change | 1 |
| Worsening | 0 |
| Drop out | 1 |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A method of treating warts of a subject, comprising administrating to said subject a pharmacologically effective amount of a composition containing an organogermanium compound having an empirical formula of $C_6H_{10}Ge_2O_7$, a minimum constitutional unit of $(O_{1/2})_3GeCH_2CH_2COOH$ and the following stereostructure:

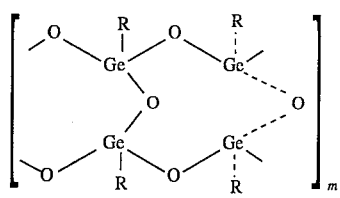

wherein R stands for $-CH_2CH_2COOH$ and m is an integer of 137±84.

2. A method according to claim 1, wherein said composition further comprises a carrier.

3. A method according to claim 2, wherein said carrier is a member selected from the group consisting of lactose, sucrose, dextran, hydroxypropylcellulose and albumin.

4. A method of treating warts according to claim 1, wherein said warts are caused by human papilloma virus.

* * * * *